(12) United States Patent
Shah et al.

(10) Patent No.: US 11,896,721 B2
(45) Date of Patent: *Feb. 13, 2024

(54) MULTIPARTICULATE L-CARNITINE COMPOSITIONS AND RELATED METHODS

(71) Applicant: Physician's Seal, LLC, Boca Raton, FL (US)

(72) Inventors: Syed M. Shah, Boca Raton, FL (US); Noreen Hassan, Boca Raton, FL (US)

(73) Assignee: Société des Produits Nestlé S.A., Vevey (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/864,715

(22) Filed: May 1, 2020

(65) Prior Publication Data

US 2020/0253882 A1 Aug. 13, 2020

Related U.S. Application Data

(60) Continuation of application No. 16/121,245, filed on Sep. 4, 2018, now Pat. No. 10,688,059, which is a division of application No. 14/476,152, filed on Sep. 3, 2014, now Pat. No. 10,085,947, which is a continuation of application No. 13/490,198, filed on Jun. 6, 2012, now Pat. No. 8,828,426.

(60) Provisional application No. 61/494,053, filed on Jun. 7, 2011.

(51) Int. Cl.
| | | |
|---|---|---|
| *A61K 31/205* | (2006.01) | |
| *A61K 9/50* | (2006.01) | |
| *A23P 10/30* | (2016.01) | |
| *A23L 33/175* | (2016.01) | |
| *A61K 31/225* | (2006.01) | |

(52) U.S. Cl.
CPC .......... *A61K 9/5073* (2013.01); *A23L 33/175* (2016.08); *A23P 10/30* (2016.08); *A61K 9/5026* (2013.01); *A61K 9/5031* (2013.01); *A61K 9/5042* (2013.01); *A61K 31/205* (2013.01); *A61K 31/225* (2013.01); *A23V 2002/00* (2013.01); *A61K 9/5078* (2013.01)

(58) Field of Classification Search
None
See application file for complete search history.

(56) References Cited

U.S. PATENT DOCUMENTS

| | | | |
|---|---|---|---|
| 5,977,162 A | 11/1999 | Seidman | |
| 6,436,946 B1 | 8/2002 | Mann | |
| 6,638,528 B1 | 10/2003 | Kanios | |
| 6,964,969 B2 | 11/2005 | McCleary | |
| 8,828,426 B2 | 9/2014 | Shah et al. | |
| 9,238,032 B2 | 1/2016 | Tabuteau | |
| 10,085,947 B2 | 10/2018 | Shah et al. | |
| 2002/0192285 A1 | 12/2002 | Mulye | |
| 2002/0192885 A1 | 12/2002 | Miyasaka | |
| 2005/0084541 A1 | 4/2005 | Nandi et al. | |
| 2005/0181047 A1* | 8/2005 | Romero | A61K 9/5078 424/469 |
| 2007/0259041 A1* | 11/2007 | Diorio | A61P 3/04 424/472 |
| 2008/0199518 A1 | 8/2008 | Ku et al. | |
| 2009/0137670 A1 | 5/2009 | Kramer et al. | |
| 2010/0093859 A1 | 4/2010 | Yamka et al. | |
| 2012/0136220 A1 | 5/2012 | Reynolds | |
| 2012/0315326 A1 | 12/2012 | Shah et al. | |

FOREIGN PATENT DOCUMENTS

RU 2008134143 A 2/2010

OTHER PUBLICATIONS

Brain Cell Support; https://cognizin.com/news/2015/brain-cell-support-plus-with-cognizin-citicoline-supports-mental-energy;2015.
Dey, et al., Multiparticulate Drug Delivery Systems for Controlled Release, Topical Journal of Pharmaceutical Research, Sep. 2008, pp. 1067-1075, Pharmacotherapy Group, Faculty of Pharmacy, University of Benin, Benin City, 300001 Nigeria.
International Search report dated Aug. 16, 2012 for PCT/US2012/41226.
International Search Report dated Aug. 2, 2017 for PCT/US17/31022.
Katarzyna Swiader et al.; "The Release of Sodium Citicoline from Enteric Coated Tablets"; Department of Experimental and Clinical Pharmacology, Medical University of Lublin, Poland; vol. XXIV, N2, 24, Section DDD; 2011; pp. 191-196.
Kim et al. (The Influence of Surelease and Sodium Alginate on the In-Vitro Release of Tamsulosin Hydrochloride in Pellet Dosage Form., J Pharm Pharmacol, Jun. 2005; 57(6): 735-42.
Science Direct; "Clarithromycin"; Tuberculosis; vol. 88(2); pp. 92-95; 2008; www.sciencedirect.com.

\* cited by examiner

*Primary Examiner* — Jake M Vu
(74) *Attorney, Agent, or Firm* — Christopher M. Ramsey; GrayRobinson, P.A.

(57) ABSTRACT

An oral controlled-release multiparticulate dosage form comprises a plurality of individually enteric coated particulates containing an L-carnitine that independently disperse in a patient's stomach after oral ingestion and travel through the stomach and past the pyloric sphincter without substantially releasing the L-carnitine in the stomach. The individual particulates contain a solid core containing the L-carnitine, and an enteric coating. The dosage form may be used to treat conditions associated with a reduction of the amount of L-carnitine in the body.

6 Claims, No Drawings

MULTIPARTICULATE L-CARNITINE COMPOSITIONS AND RELATED METHODS

CROSS-REFERENCE TO RELATED APPLICATIONS

This is a continuation of application Ser. No. 16/121,245, filed Sep. 4, 2018, which is a divisional of application Ser. No. 14/476,152, now U.S. Pat. No. 10,085,947, filed Sep. 3, 2014, which is a continuation of application Ser. No. 13/490,198, now U.S. Pat. No. 8,828,426, filed Jun. 6, 2012, which claims priority to U.S. provisional Application No. 61/494,053, filed Jun. 7, 2011, which are all incorporated by reference herein in their entireties.

FIELD OF THE INVENTION

This relates to multiparticulate compositions comprising the active ingredient L-carnitine or a derivative thereof, and more particularly, to controlled release multiparticulate formulations comprising L-carnitine or a derivative thereof and related methods.

BACKGROUND

L-Carnitine is a naturally occurring compound that facilitates the transport of fatty acids into the mitochondria for oxidation, and thereby energy production. It is a derivative of the amino acid lysine. Acetyl L-Carnitine (ALCAR) is an acetylated derivative of L-Carnitine.

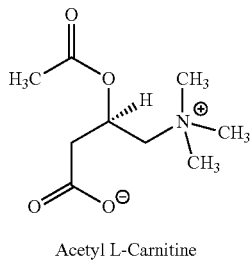

Acetyl L-Carnitine

L-carnitine and its derivatives are used to treat carnitine deficiency, age related decline in mitochondrial function, cardiovascular disease (myocardial infarction, heart failure and angina pectoris), intermittent claudication, end-stage renal failure, Alzheimer's disease, HIV/AIDS and decreased sperm motility. In humans, the endogenous carnitine pool comprises free L-carnitine and a range of short-, medium- and long-chain esterified carnitine derivatives, including acetyl-L-carnitine and propionyl-Lcarnitine, for example. As a supplement taken orally, ALCAR has better bioavailability, than L-carnitine. Therefore, the esterified forms of L-carnitine may be considered as prodrugs of L-carnitine.

Unfortunately, some of the current techniques for administering L-carnitine or its ester prodrugs to patients present several problems. Since L-carnitine and the derivatives ALCAR and propionyl-L-carnitine can cause various side effects such as upset stomach, nausea and vomiting, it is desirable to administer L-carnitine, ALCAR, or propionyl-L-carnitine in a manner that minimizes the manifestation of these side effects. Current administration techniques are hampered in this regard because they present a small therapeutic window between when the benefits of L-carnitine, acetyl-L-carnitine, or propionyl-L-carnitine take effect and when the side effects are manifested.

SUMMARY

In view of the foregoing, it is an object of the invention to provide a controlled-release L-carnitine based composition that is adapted to minimize the side effects caused by carnitine, and provides for less frequent, more predictable, and reliable dosing by allowing carnitine to pass through the stomach more quickly and to be dispersed throughout the intestinal tract.

In a composition aspect of the invention, a carnitine composition comprises a plurality of independently dispersible particulates, each independently dispersible particulate comprising: a spheroidal core comprising about 30%-90% w/w of a carnitine, about 15%-70% w/w microcrystalline cellulose, and about 0.5%-1.5% w/w hydroxypropyl methylcellulose; a sub-coat on the spheroidal core, the subcoat comprising hydroxypropyl methyl cellulose present in an amount of about 2%-4% w/w of the independently dispersible particulates; and an enteric coat on the sub-coated spheroidal core, the enteric coat being about 5%-15% w/w of the independently dispersible particulates; wherein the average diameter of the independently dispersible particulates is about 0.1-3 mm.

The enteric coat may be selected from methacrylic acid co-polymer, cellulose acetate phthalate, polyvinyl acetate phthalate, or a combination thereof. Alternatively, the enteric coat may comprise a polymeric material that forms a film around the core and a pore former material that generates pores in the film under intestinal pH conditions. In a particular embodiment, the polymeric material is ethyl cellulose and the pore former material is sodium alginate.

In some embodiments, the composition further comprises a carnitine permeation enhancer adapted to assist the carnitine to permeate biological tissue. In a particular embodiment, the carnitine permeation enhancer is a p-glycoprotein efflux pump inhibitor such as, for example, polysorbate 80.

In some embodiments, the core further comprises a pellet, wherein the carnitine is located on an outer surface of the pellet. The pellet may be a non-pareil pellet or microcrystalline cellulose pellet, for example.

The composition is preferably present in a pharmaceutically acceptable dosage form for being administered to a patient.

In a method of use aspect of the invention, a method of treating a physiological condition in a patient comprises administering the composition of the invention to the patient. In a preferred embodiment, the physiological condition is selected from carnitine deficiency, age related decline in mitochondrial function, cardiovascular disease, myocardial infarction, heart failure, angina pectoris, intermittent claudication, end-stage renal failure, Alzheimer's disease, HIV/AIDS, decreased sperm motility, or a combination thereof. Administering the composition to the patient may comprise administering a capsule having the independently dispersible particulates therein, combining the composition with an acidic food vehicle, or providing a blend of the composition and an acidic food vehicle to the patient through a feeding tube.

In a method of making aspect of the invention, a method of making a controlled-release multiparticulate composition of L-carnitine comprises: producing a spheroidal core comprising about 30%-90% w/w of a carnitine, about 15%-70% w/w microcrystalline cellulose, and about 0.5%-1.5% w/w hydroxypropyl methylcellulose; coating the spheroidal core with a sub-coat comprising hydroxypropyl methylcellulose, the sub-coat being about 2%-4% w/w of the particulates in the multiparticulate composition; applying an enteric coat to the sub-coated spheroidal core, the enteric coat being about 5%-15% w/w of the particulates in the multiparticulate composition; and wherein the average diameter of particulates in the multiparticulate composition is about 0.1-3 mm.

In some embodiments, the spheroidal core is produced by extrusion and spheronization. In a particular example, the spheroidal core is produced by blending the carnitine, microcrystalline cellulose, and hydroxypropyl methylcellulose with water to form a met mass and extruding the wet mass, cutting the extruded wet mass into pieces, spheronizing the pieces, and drying the spheronized pieces. The spheronized pieces are preferably dried at a temperature of about 50° C.-60° C.

In some embodiments, the spheroidal core is produced by coating a non-pareil or microcrystalline cellulose pellet with the carnitine, microcrystalline cellulose, and hydroxypropyl methylcellulose.

These and other objects, aspects, and advantages of the present invention will be better appreciated in view of the following detailed description of the invention.

DETAILED DESCRIPTION OF PREFERRED EMBODIMENTS

In the Summary above and in the Detailed Description, reference is made to particular features including method steps of embodiments of the invention. Where a particular feature is disclosed in the context of a particular aspect or embodiment of the invention, that feature can also be used, to the extent possible, in combination with and/or in the context of other particular aspects and embodiments of the invention, and in the invention generally.

The term "comprises" is used herein to mean that other ingredients, steps, etc. are optionally present. When reference is made herein to a method comprising two or more defined steps, the steps can be carried in any order or simultaneously (except where the context excludes that possibility), and the method can include one or more steps which are carried out before any of the defined steps, between two of the defined steps, or after all of the defined steps (except where the context excludes that possibility).

In this section, the present invention will be described more fully, in which preferred embodiments of the invention are detailed. This invention may, however, be embodied in many different forms and should not be construed as limited to the embodiments set forth herein. Rather, these embodiments are provided so that this disclosure will be thorough and complete, and will convey the scope of the invention to those skilled in the art.

One aspect of the invention is to provide multiparticulate compositions comprising L-carnitine or an L-carnitine derivative for treating physiological disorders related to a reduction of L-carnitine in the body of a patient. As used herein, the term "L-carnitine" refers to L-carnitine and its esterified derivatives including acetyl-L-carnitine and propionyl-L-carnitine unless the context suggests otherwise. Examples of physiological disorders that may be treated with such a multiparticulate composition include L-carnitine deficiency, age related decline in mitochondrial function, cardiovascular disease (myocardial infarction, heart failure and angina pectoris), intermittent claudication, end-stage renal failure, Alzheimer's disease, Parkinson's disease, Peyronie's disease, insulin response deficiencies, HIV/AIDS, peripheral nerve injury, spinal cord injury, and decreased sperm motility.

Multiparticulate compositions of the invention advantageously permit the particulates in the composition to pass to the intestines without substantially releasing L-carnitine in the stomach, thus preventing the undesirable side effects or reduced efficacy of L-carnitine that may result otherwise.

Further, because it is desirable for L-carnitine to be released into the intestines as opposed to the stomach, the composition provides reduced release in the stomach and an elevated release at a substantially neutral pH, such as the pH found in the intestines. As used herein, a substantially neutral pH environment means an environment having a pH of about 7, including, but not limited to a pH of between about 6.5 to about 7.5, also including the pH environment of the intestines.

The L-carnitine multiparticulate compositions of the invention provide an advantageous L-carnitine non-parenteral delivery vehicle that can be administered to a patient. A multiparticulate composition of the invention comprises a plurality of individual particulates that are preferably spheroidal in shape and are preferably configured for incorporation into a capsule or packet-type oral delivery dosage form.

The multiparticulates of the invention comprise a plurality of particulates which are preferably spheroidal in shape. Each particulate is sized to fit through the pyloric sphincter in a relaxed state. The diameter of the particulates is preferably in the range of about 0.1-3 mm, more preferably about 1-2.5 mm.

In certain embodiments, the particulates comprise a preferably spheroidal core with an enteric coating over the core. The particulates may also have an optional sub-coating between the core and enteric coating. In a preferred embodiment, the sub-coating comprises hydroxypropyl methyl cellulose, also known as "HPMC" or "hypromellose." The particulates may also include one or more additional coatings such as a sealant coating or a color coating over the enteric coating.

The core comprises the primary active ingredient, an L-carnitine. In preferred embodiments, the L-carnitine is L-carnitine itself, acetyl-L-carnitine, and/or propionyl-L-carnitine. The core may also comprise one or more inactive ingredients.

The core may also include one or more of filler, stabilizer, binder, surfactant, processing aid, or disintegrant. By way of example only, suitable materials for performing these functions are provided. A suitable filler includes a pharmaceutically suitable filler. In one embodiment, the filler is microcrystalline cellulose. A suitable binder includes a pharmaceutically suitable binder. In a preferred embodiment, the binder is a cellulosic water soluble polymer such as cellulose ether. In one embodiment, a surfactant is added as a solubilizing agent, such as polysorbate 80. A suitable processing aid includes a pharmaceutically suitable processing aid such as for improving the flowability of the core materials during processing. In a preferred embodiment, the processing aid is colloidal silicon dioxide. A suitable disintegrant includes a pharmaceutically suitable disintegrant. In one embodiment, the disintegrant is croscarmellose sodium.

A preferred composition for the core comprises about: 30-90% w/w of an L-carnitine; about 1% to 15% w/w processing aid; about 15 to 60% w/w filler; about 4% to 6% w/w disintegrant; about 0.5% to 15% w/w binder; about 1% to 3% w/w solubilizing agent; and about 0.5% to 4% w/w antioxidant. Here the % w/w is relative to the total weight of the particulate core.

A listing of ingredients for an exemplary embodiment of the core is shown in Table 1. In Table 1, the % w/w is based on the uncoated core. For the core, L-carnitine was supplied as 98% w/w L-carnitine/2% w/w Cab-O-Sil M5P (Silicon Dioxide) and was milled using a granulation mixer. The % represents the theoretical quantity of L-carnitine in the blend. The core utilizes AVICEL Ph102 as the filler.

The sub coating is a solution applied over the core. The sub coating is preferably an additional layer of binder, such as from an about 10% Hypromellose solution.

The enteric coating is applied over the uncoated core or, if the sub-coating is present, over the sub-coating. The enteric coating is preferably applied so that it comprises about 5-35% w/w of the enteric coated particulate. A preferred enteric coating material is a methacrylic acid based material such as a methacrylic acid-based co-polymer. Examples of suitable methacrylic acid based copolymers include EUDRAGIT L30D-55 or KOLLICOAT MAE 30 DP. These materials may be combined with other materials such as plasticizers for forming an enteric coating solution. In a typical embodiment, an enteric coating solution comprises about 20-70% w/w water, about 0.5-1.5% w/w plasticizer, about 3-15% anti-adherent, and about 25-70% copolymer. By way of example only, a suitable plasticizer is triethyl citrate and a suitable anti-adherent is PlasACRYL T20.

A listing of the ingredients in an exemplary embodiment of enteric coated particulates is provided in Table 2. The % w/w is based on the weight of solution applied to the particulate.

Methods of making the multiparticulate compositions in accordance with another aspect of the invention will now be described. The core is typically prepared by wet granulating the core materials into a wet mass, extruding the wet mass to form an extrudate, cutting the extrudate into a plurality of core pieces, and spheronizing the core pieces. The spheronized core pieces are preferably dried to <3% based on the Karl Fischer method. The spheronized core pieces are then coated with the enteric coating material, which is typically applied in a fluidized bed coater. The enteric coated particulates are subsequently dried, to <3% (Karl Fischer). The dried enteric coated multiparticulates may then be prepared into a suitable pharmaceutical dosage form such as a capsule or tablet, for example. A typical preferred capsule contains about 1000 mg of the particulates. Depending on the desired dosage, however, this may be adjusted.

The multiparticulate compositions of the invention are preferably formulated to be taken orally by a human or animal patient and to ensure that the patient receives an effective amount of L-carnitine over the course of several hours after ingestion. An effective amount is an amount that is sufficient to affect a disease or process in the body. In a preferred embodiment a dose of a multiparticulate composition provides about 1000 mg to 3000 mg or, more preferably, about 2000 mg of L-carnitine. Doses of the multiparticulate composition may be administered sporadically. A patient may be a human or animal patient.

Accordingly, another aspect of the invention is to provide a method of treating at least one of carnitine deficiency, age related decline in mitochondrial function, cardiovascular disease (myocardial infarction, heart failure and angina pectoris), intermittent claudication, end-stage renal failure, Alzheimer's disease, HIV/AIDS and decreased sperm motility, the method comprising administering a multiparticulate composition of the invention to the patient.

The multiparticulate compositions of the invention are preferably formulated to be taken non-parenterally by a patient for treating one or more physiological conditions that can be remediated by L-carnitine and derivatives thereof. In a method of use aspect of the invention, a method of treating a physiological condition in a patient comprises administering a composition of the invention to the patient. The term "patient" refers to humans or other animals considered as having one or more physiological conditions that can be remediated with L-carnitine and derivatives thereof. Examples of such physiological conditions include serotonin deficiency, depression, weight loss, headaches, fibromyalgia, cerebellar ataxia, and insomnia. The term "administering" refers to the giving or applying of a substance. In a preferred embodiment, administering the composition to the patient includes administering a capsule having the independently dispersible particulates therein.

In another preferred embodiment, administering the composition to the patient includes combining the independently dispersible particulates with an acidic food vehicle, such as an acidic, semi-solid food or drink. This administration technique may be particularly useful with patients who have difficulty swallowing. In such embodiments, the particulates are preferably loaded into a sachet that the patient or a caregiver can easily open for sprinkling the particulates onto the acidic food vehicle. When the patient ingests the acidic food vehicle, the patient also ingests the particulates. Preferred acidic food vehicles include food products like applesauce, fruit slurries, fruit juices, or the like. In one embodiment of the invention, the independently dispersible particulates are administered to a patient using a feeding tube such as a gastric feeding tube, nasogastric feeding tube, or jejunostomy feeding tube.

Doses of the multiparticulate composition may be administered sporadically when needed or may be administered as part of a long term treatment.

These embodiments of the invention have many advantages. Some but not all of those advantages are listed here. Not all of the advantages are required by all embodiments of the invention.

One advantage of the multiparticulate compositions of the invention is that they will provide a more reliable release of L-carnitine and derivatives thereof when compared to single-unit sustained release formulations that are presently available, without concern for dosing of the patient under the fed or fasted state. They will further provide a prolonged exposure to the L-carnitine and derivatives thereof both locally and systemically as compared to the single-unit sustained release formulations. The use of multiparticulate formulations of the present invention comprising L-carnitine and derivatives thereof may allow for less frequent dosing and may also allow for dosing with a lower total amount of L-carnitine and derivatives thereof. Dispersion of the particulates in the lumen of the small bowel, prior to release of the L-carnitine, may reduce the incidence of side effects seen with the other carnitine formulations. Further, single unit sustained release formulations tend to release the L-carnitine and derivatives thereof only in the local vicinity of the dosage form. The multiparticulate compositions of the present invention can avoid this problem because the particulates will disperse in the intestinal tract to provide a delocalized dose of L-carnitine and derivatives thereof therein.

Example

This section describes an example of a preferred embodiment of the invention. The example is not intended to limit the scope of the invention in any way.

TABLE 1

Ingredients of an exemplary embodiment of the core.

| Ingredient | (grams/% w/w) | Ingredient Function |
|---|---|---|
| L-Carnitine | 935.9/78.4 | Active ingredient |
| CAB-O-SIL M5P (Colloidal Silicon Dioxide) | 19.1/1.6 | Processing Aid |
| AVICEL (Micro Crystalline cellulose) | 227.0/19.0 | Filler |
| Hypromellose (Methocel A15 Premium) | 11.9/1.0 | Binder |
| Water (% of dry mass) | (15.0%) | |

TABLE 2

Ingredients of an exemplary embodiment of enteric-coated particulates.

| Ingredient | (grams/% w/w) | Ingredient Function |
|---|---|---|
| KOLLICOAT MAE 30 DP Solids | 506.6/85.8 | Source of methacrylic copolymer |
| Triethyl Citrate | 75.7/12.8 | Plasticizer |
| PLASACRYL T20 | 7.9/1.3 | Anti-Adherent |
| Water[1] | | |

[1]Evaporates

Example: Preparation of Multiparticulate Compositions

Experimental Details. The equipment utilized to create the compositions herein includes the following: top loading balances, hand screens (12, 14, 16, 18, Pan, 70 mesh), Rotap sieve shaker, IKA mixer, KitchenAid food processor (pre-milling), Hobart mixer, LCI Benchtop Granulator, Fitz mill equipped with a 0.065" screen, Jet Mill, Key International high sheer mixer, Glatt GPCC-3 fluid bed drier, Glatt GPCC-3 fluid bed dried with 7" Wurster, Karl Fischer moisture analyzer, and a spheronizer.

Acetyl L-Carnitine pre-conditioning. The Acetyl-L-Carnitine raw material contained large clumps of fine crystals. Also, the material is hygroscopic. It is necessary to de-lump the raw material and reduce the hygroscopicity in order to process the material. 500 g Acetyl-L-Carnitine (Lonza ALC Carnipure) and 10.2 grams CAB-O-SIL M5P (Cabot Corporation) were blended for 1-5 minutes in a KitchenAid Food Processor equipped with blade or similar blender and equipped with intensifier bar or pin bar.

Preparation of Core. The core was prepared utilizing the following steps and settings. 955 grams ALCAR/SiO$_2$ (98/2% w/w), 227 grams Microcrystalline Cellulose (Avicel Ph 102; FMC Corporation), and 11.9 grams Methocel A15 LV (Dow) were low shear granulated in a 0.5 Gallon (2 Liter) Hobart or other granulation mixer and mixed at low speed for about 5 minutes. About 162-172 g USP water was sprayed into the mixer to achieve peak granulation moisture of about 12% to about 12.6% w/w, and this was blended for about an additional 10-30 minutes to form a wet mass.

The wet mass was extruded through a 1.0 mm-hole perforated metal screen using a LCI Benchtop Granulator at speed setting 10.

The extrudate was spheronized in 25-30 grams sub lots using a Caleva Model 120 spheronizer equipped with a small pyramid plate at high speed for 2-3 minutes.

The combined spheronization sub lots (~1373 grams) were dried in a GPCG-3 or similar fluid bed dryer for about 45 minutes with an inlet temperature set point of 50° C. and a process air flow of 60 cfm.

The finished dried ALCAR multiparticulates were collected between 12-mesh and 18-mesh screens resulting in a loose Bulk Density of about 0.68 g/cc. A Camsizer particle size distribution analysis was performed finding a size distribution of: $DV_{10}$ 1.002 mm, $DV_{50}$ 1.177 mm, and $DV_{90}$ 1.405 mm; a specific surface area (Sv) of 5.132/mm; and a specific surface srea (Sm) of 75.923 cm$^2$/g.

Application of sub-coating. 1000 grams of ALCAR particulates were separated based on their size. The fraction that fell within the 14-18 mesh size were chosen for sub-coating. The cores were placed into a Glatt GPCC-3 fluid bed drier and the sub-coating was sprayed onto the cores in the form of a 10% hypromellose (hypromellose E5) aqueous solution that was at room temperature.

The sub-coating solution (306 g USP Water (T>55° C.) and 34 g hypromellose E5) was applied to the cores using the following parameters: the inlet temperature was maintained at about 50° C.; the air flow was maintained at about 50 cfm; the spray rate was maintained between 6.0 and 11.0 g/min; and the filter shake cycle was 45/3 seconds (Time Between Shaking/Shaking Time). The fluid bed drier was setup with a 1.0 mm Schlick 970 nozzle port, and 2×360 air cap setting, a 1.5 cm partition setting, and a multiparticulate bottom plate or equivalent.

Preparation of enteric coating solutions. The enteric coatings were applied to the cores in a fluidized bed coater (7" wurster) as a liquid solution. The formula for the enteric coating was 1160 grams USP Water (RT), 506.6 grams BASF KOLLICOAT MAE 30 DP, 75.7 grams PLASACRYL T20 (Colorcon), and 7.9 grams triethyl citrate USP, which was mixed a minimum of 20 minutes and screen through a 40-mesh screen prior to use.

The enteric coating solution was applied to 1000 grams of ALCAR particulate cores using the following parameters: the inlet temperature was maintained at about 50° C.; the air flow was maintained at about 50 cfm; the spray rate was maintained between 6.0 and 11.0 g/min; the atomization air pressure was maintained at about 2.0 bar; and the filter shake cycle was 45/3 seconds (Time Between Shaking/Shaking Time). The fluid bed drier was set up with a 1.0 mm Schlick 970 nozzle port, and 2×360 air cap setting, a 1.5 cm partition setting, and a multiparticulate bottom plate or equivalent.

A finish coat may be applied over the enteric coating, and is applied in a same or similar manner as the enteric coating.

Unless otherwise defined, all technical and scientific terms used herein are intended to have the same meaning as commonly understood in the art to which this invention pertains and at the time of its filing. Although various methods and materials similar or equivalent to those described herein can be used in the practice or testing of the present invention, suitable methods and materials are described. The skilled should understand that the methods and materials used and described are examples and may not be the only ones suitable for use in the invention.

Any publications, patent applications, patents, and other references mentioned herein are incorporated by reference in their entirety as if they were part of this specification. However, in case of conflict, the present specification, including any definitions, will control.

In the specification set forth above there have been disclosed typical preferred embodiments of the invention, and although specific terms are employed, the terms are used in a descriptive sense only and not for purposes of limitation.

The invention has been described in some detail, but it will be apparent that various modifications and changes can be made within the spirit and scope of the invention as described in the foregoing specification.

That which is claimed is:

1. An oral controlled-release multiparticulate dosage form comprising an L-carnitine carried on a plurality of individually enteric coated particulates that independently disperse in a person's stomach after oral ingestion and travel through the stomach and past a pyloric sphincter, the individually enteric coated particulates comprising (a) a spheronized extrudate solid core including the L-carnitine intermixed with a pharmaceutically acceptable binder and a pharmaceutically acceptable filler and (b) an enteric coating over the solid core, a predominant component of the enteric coating being an enteric polymer, wherein the solid core is spheroidal and comprises 30%-90% w/w of the L-carnitine, 15%-70% w/w microcrystalline cellulose filler, and 0.5%-1.5% w/w hydroxypropyl methylcellulose binder.

2. The dosage form of claim 1, wherein the L-carnitine is selected from at least one of L-carnitine, acetyl-L-carnitine, and propionyl-L-carnitine.

3. The dosage form of claim 1, wherein the enteric polymer is selected from at least one of methacrylic acid co-polymer, cellulose acetate phthalate, and polyvinyl acetate phthalate.

4. The dosage form of claim 1, wherein an average diameter of the individually enteric coated particulates is about 0.1-3 mm.

5. The dosage form of claim 1, further comprising a cellulosic water soluble polymer subcoating over the solid core and under the enteric coating.

6. The dosage form of claim 1, further comprising polysorbate 80 effective to enhance permeation of the L-carnitine in a person's tissue.

* * * * *